(12) United States Patent
Kreindel

(10) Patent No.: US 11,291,499 B2
(45) Date of Patent: Apr. 5, 2022

(54) DEVICE AND METHOD FOR TREATMENT OF SLEEP DISORDERS

(71) Applicant: Inmode Ltd., Yokneam (IL)

(72) Inventor: Michael Kreindel, Richmond Hill (CA)

(73) Assignee: Inmode Ltd., Yokneam (IL)

( * ) Notice: Subject to any disclaimer, the term of this patent is extended or adjusted under 35 U.S.C. 154(b) by 213 days.

(21) Appl. No.: 15/854,141

(22) Filed: Dec. 26, 2017

(65) Prior Publication Data

US 2019/0192219 A1 Jun. 27, 2019

(51) Int. Cl.
| | |
|---|---|
| *A61B 18/14* | (2006.01) |
| *A61B 18/12* | (2006.01) |
| *A61B 18/00* | (2006.01) |
| *A61F 5/56* | (2006.01) |
| *A61N 1/36* | (2006.01) |
| *A61B 17/24* | (2006.01) |

(52) U.S. Cl.
CPC ...... *A61B 18/1492* (2013.01); *A61B 18/1206* (2013.01); *A61B 18/1485* (2013.01); *A61B 2017/248* (2013.01); *A61B 2018/00321* (2013.01); *A61B 2018/00327* (2013.01); *A61B 2018/00642* (2013.01); *A61B 2018/00702* (2013.01); *A61B 2018/00761* (2013.01); *A61B 2018/00791* (2013.01); *A61B 2018/00815* (2013.01); *A61B 2018/00821* (2013.01); *A61B 2018/1467* (2013.01); *A61F 5/56* (2013.01); *A61N 1/3601* (2013.01)

(58) Field of Classification Search
CPC .............. A61B 18/492; A61B 18/1206; A61B 2017/248; A61B 18/14; A61B 18/1485; A61B 2018/1467; A61B 2018/1472; A61B 2018/1497; A61B 2018/162; A61B 2018/165; A61B 2018/126; A61B 2018/00791; A61B 2018/00642; A61B 2018/00321; A61B 2018/00327; A61B 2018/00702; A61B 17/24; A61F 5/56; A61F 5/566; A61N 1/3601
USPC ........ 606/41, 42, 45, 46, 48–50; 607/98, 99, 607/101, 102, 113, 115, 116, 134
See application file for complete search history.

(56) References Cited

U.S. PATENT DOCUMENTS

| | | | | |
|---|---|---|---|---|
| 4,202,337 A | * | 5/1980 | Hren .................. | A61B 18/1402 606/48 |
| 6,086,585 A | * | 7/2000 | Hovda ............... | A61B 18/1402 606/45 |
| 6,126,657 A | * | 10/2000 | Edwards ................ | A61B 17/24 606/45 |
| 6,632,193 B1 | * | 10/2003 | Davison ............. | A61B 18/1485 604/22 |
| 2002/0156470 A1 | * | 10/2002 | Shadduck ............. | A61N 1/326 606/41 |

(Continued)

*Primary Examiner* — Thomas A Giuliani
(74) *Attorney, Agent, or Firm* — Dekel Patent Ltd.; David Klein

(57) ABSTRACT

A method includes inserting a distal end of an applicator and delivering RF energy inside a mouth, applying one or more electrodes to a treatment area inside the mouth, and applying RF energy to the treatment area to increase its temperature. The method includes measuring tissue surface temperature in the treatment area with a temperature sensor; and adjusting RF energy automatically to achieve collagen remodeling and avoid tissue coagulation or ablation and thereby treat a sleep obstructing disorder.

12 Claims, 3 Drawing Sheets

(56) References Cited

U.S. PATENT DOCUMENTS

| | | | |
|---|---|---|---|
| 2012/0071870 A1* | 3/2012 | Salahieh | A61B 5/287 |
| | | | 606/33 |
| 2012/0136347 A1* | 5/2012 | Brustad | A61B 18/1445 |
| | | | 606/33 |
| 2013/0304052 A1* | 11/2013 | Rizq | A61B 18/18 |
| | | | 606/33 |
| 2018/0177546 A1* | 6/2018 | Dinger | A61B 18/1485 |

* cited by examiner

DEVICE AND METHOD FOR TREATMENT OF SLEEP DISORDERS

FIELD OF THE INVENTION

The invention relates to a device in the field of RF treatment to remodel collagenous tissue in the mouth for treatment sleep disorders.

BACKGROUND OF THE INVENTION

There are many surgical methods to treat sleeping disorders, such as snoring and sleep apnea. U.S. Pat. Nos. 5,707,349, 5,817,049, 5,820,580, 6,416,491 describe devices for debulking interior parts of the tongue. At least one electrode is advanced into the interior of the tongue and delivers electromagnetic energy to ablate the tissue without damaging hypoglossal nerves. U.S. Pat. No. 6,045,549 describes a minimally invasive ablative device for treating the upper airway. U.S. Pat. No. 6,086,585 describes a device for removing tissue in the throat using RF energy in presence of conductive fluids for treatment sleep obstructive disorders. U.S. Pat. No. 6,126,657 describes a device for ablating the interior tissue of tongue to treat sleep disorders. U.S. Pat. No. 6,159,208 describes a device for treating sleeping disorders by ablation tissue surface using RF energy and multiple electrodes. U.S. Pat. No. 6,296,636 describes an RF power supply controlling RF power applied to the tissue in presence of conductive fluid for treatment in the mouth.

Alternatively, U.S. Pat. No. 6,632,193 describes a method for applying electrical energy to a body structure including the throat comprising positioning a first electrode adjacent to or in contact with a body structure; positioning a second electrode in the region of the body structure; electrically insulating the first and second electrodes from each other; and applying a sufficient high frequency voltage difference between the first and second electrodes to modify at least a portion of the body structure including collagen contraction.

SUMMARY OF THE INVENTION

The present invention is directed to a device and method for delivery RF energy to the tissue surface inside the mouth and throat. The device includes a hand piece having a handle at the proximal end and a disposable tip at the distal end. The disposable tip has one or more electrodes to apply RF energy to the tissue surface. At least one of the electrodes has a thin surface with a thermal sensor attached to it and has a response time of less than 2 sec. The hand piece is connected to an RF generator providing RF energy to the electrodes.

The device has a user interface for setting one or more of the following treatment parameters:
RF power
Treatment time
Tissue target temperature Alternatively, parameters can be preset automatically by the controller and applied when the user activates the energy.

A single use disposable tip may be used either in mono-polar or bi-polar mode. The number of electrodes in the tip may be optimized to create a uniform heating field. The electrodes may be made from metal with a thickness less than 1 mm to efficiently transfer heat to the other side to the temperature sensor. Alternatively, the electrode may have a hole for temperature sensor to be in direct surface with the treated surface. Without limitation, thermistors or thermo- couples may be used as the temperature sensor. Alternatively, optical sensors can be used for temperature measurements.

The device measures and controls RF current, voltage, power and tissue impedance. RF power delivered to the tissue may be adjusted according to temperature measurements to reach and maintain the required tissue temperature. The typical temperature range to achieve collagen remodeling without tissue necrosis is in the range of 40° C. to 50° C.

In another embodiment, the electrodes applied to the treated area may be cooled to protect the surface from overheating.

The RF power applied to the tissue depends on the electrode size to balance the tissue heating speed with temperature sensor response time. RF power can be delivered in continuous wave (CW) or quasi-CW manner during treatment time. Tissue impedance may be monitored to insure proper contact between tissue and electrodes. A water-based gel may be used to improve coupling.

A non-limiting range of parameters is as follows:
Treated spot size—1-5 $cm^2$
RF power—5-40 W
RF frequency 0.2-10 MHz
Sensor response time 0.1-1 sec

DETAILED DESCRIPTION OF THE INVENTION

Figure 1:
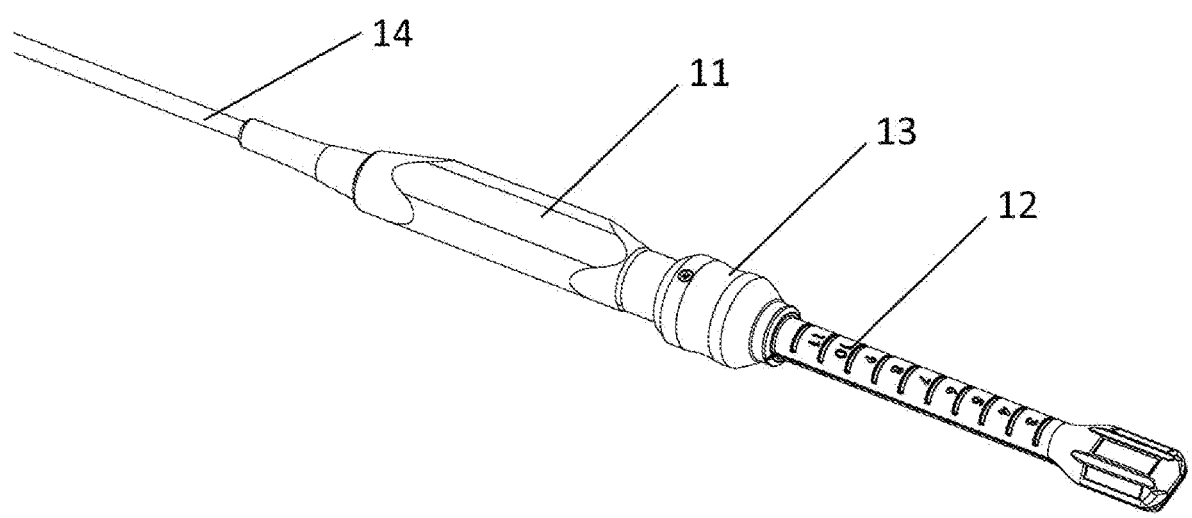
FIG. 1 is a schematic illustration of a hand piece with a disposable tip, in accordance with a non-limiting embodiment of the invention.

Referring first to FIG. 1, an applicator assembly includes a handle 11. A disposable tip 12 is connected to the handle 11. Handle 11 has a locking mechanism 13 fixing the disposable tip 12 to handle 11. All communication of signals and power between handle 11 and an external device (which includes RF power source and processing circuitry) may be via a cable 14. The RF power source provides RF power to the handle 11 through the cable 14, and a temperature sensor signal from the disposable tip is delivered to the processing circuitry through the same cable 14 or by wireless communication.

Figure 2:
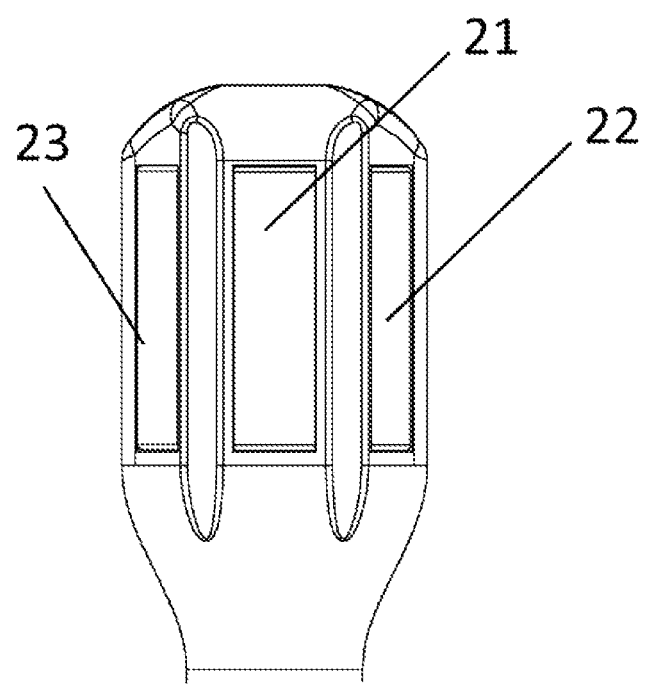
FIG. 2 is a schematic illustration of electrodes, in accordance with a non-limiting embodiment of the invention.

FIG. 2 illustrates the electrode geometry on the disposable tip 12. In the non-limiting illustrated embodiment, there are three electrodes: a central electrode 21 has one polarity while two side electrodes 22, 23 have the opposite polarity. The size of the electrodes and the distance between them are designed to have virtually uniform distribution of RF energy in the tissue. Size and shape of the tip are optimized to have good contact with treated tissue, such as the soft palate and tongue.

Figure 3:
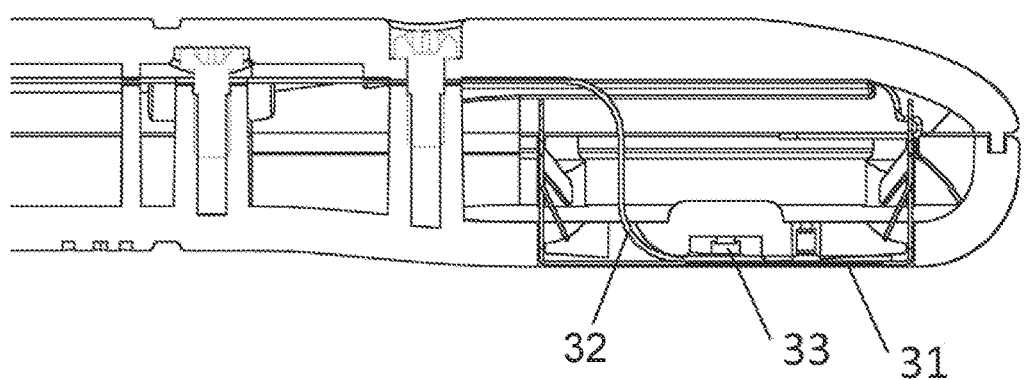
FIG. 3 is a cross-sectional illustration of a disposable tip, in accordance with a non-limiting embodiment of the invention.

Referring to FIG. 3, a cross-section of the disposable tip is shown. Without limitation, the electrode 31 may be made from thin stainless steel sheet with a thickness of about 0.2 mm. Electrode 31 contacts the tissue, delivering RF energy to the treated site. A flexible PCB 32 is attached to the opposite side of electrode 31 having good thermal contact with the electrode 31. The thickness of flexible PCB 32 may be, without limitation, about 100 microns. A miniature SMD (surface mount device) thermistor 33 may be soldered to the opposite side of PCB 32 and senses skin temperature through the thin electrode 31 and PCB 32. Thermistor 33 is fast enough to prevent tissue overheating. Typical response time is, without limitation, about 0.3 sec.

Figure 4:
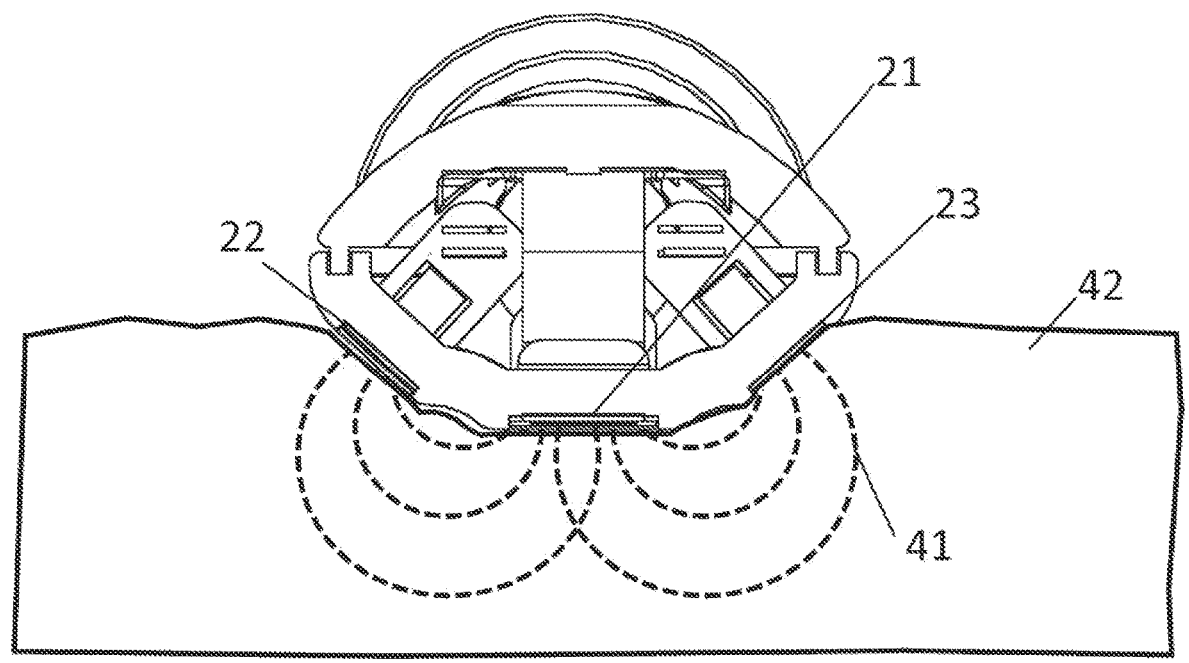
FIG. 4 is a schematic illustration of RF energy between electrodes, in accordance with a non-limiting embodiment of the invention.

FIG. 4 illustrates RF energy distribution 41 between electrodes. RF current goes from central electrode 21 having one polarity to the side electrodes 22, 23 having opposite polarity. Central electrode 21 may have a larger area than side electrodes 22, 23 to have uniform current density and heating in the treated tissue 42.

Non-limiting parameters for the device are as follows:
1. Length of disposable tip may be 7-20 cm
2. Tip treatment area may be 0.5-5 cm$^2$
3. Number of electrodes on the tip may be two or more for bipolar design. Alternatively, a mono-polar design can be used with a separate return electrode.
4. Average RF power may be in the range of 5 W to 40 W which can be delivered in CW or quasi-CW mode
5. Frequency of RF may be from 0.2 M Hz up to 10 MHz
6. Treatment time may be in the range of 10 sec up to 20 min.
7. RF voltage may be applied to the skin in the range of 10V up to 1000V
8. Temperature sensor response time may be from 0.1 sec up to 2 sec.

The invention claimed is:

1. A method comprising: applying an applicator to a treatment area inside a mouth, said applicator comprising a central electrode which has a first polarity and left and right side electrodes which have a polarity opposite to the first polarity, wherein said central electrode is disposed flush on a flat mouth-tissue contacting surface of said applicator and all portions of said left and right side electrodes are disposed flush on respective left and right flat surfaces that are tilted with respect to a plane defined by said flat mouth-tissue contacting surface, and said applicator further comprises respective left and right arcuate surfaces, both tilted with respect to the plane defined by said flat mouth-tissue contacting surface, which respectively separate said left and right flat surfaces from said flat mouth-tissue contacting surface; using said electrodes to apply RF energy to the treatment area to increase its temperature; measuring tissue surface temperature in the treatment area with a temperature sensor; and adjusting RF energy to achieve collagen remodeling and avoid tissue coagulation or ablation and thereby treat a sleep obstructing disorder.

2. The method according to claim 1 wherein the treatment area is a tongue or a soft palate.

3. The method according to claim 1 wherein the sleep obstructing disorder is snoring or sleep apnea.

4. The method according to claim 1, wherein tissue of the treatment area is heated up to 40° C. to 50° C.

5. The method according to claim 1, wherein frequency of the RF energy is in a range of 100 kHz to 10 MHz.

6. The method according to claim 1, wherein the RF energy is applied in CW manner.

7. The method according to claim 1, wherein average RF power is 1-50 W.

8. The method according to claim 1, wherein the collagen remodeling causes tissue contraction.

9. The method according to claim 1, wherein the temperature sensor comprises a thermistor, a thermocouple or an optical sensor.

10. The method according to claim 1, wherein a thermal response time of the temperature sensor is in a range of 0.1 sec to 2 sec.

11. The method according to claim 1, wherein said central electrode has a larger area than said side electrodes.

12. The method according to claim 1, wherein said central electrode is made from a metal sheet having a contact surface and a flexible printed circuit board is attached to said central electrode on a side opposite to said contact surface, and said temperature sensor is part of circuitry of said flexible printed circuit board.

* * * * *